US008309688B2

(12) United States Patent
Cotty et al.

(10) Patent No.: US 8,309,688 B2
(45) Date of Patent: Nov. 13, 2012

(54) MONKEY HOMOLOG OF HUMAN ONCOSTATIN M AND METHODS OF USE THEREOF

(75) Inventors: Adam Cotty, Radnor, PA (US); Michael Naso, Radnor, PA (US)

(73) Assignee: Centocor Ortho Biotech Inc., Horsham, PA (US)

(*) Notice: Subject to any disclaimer, the term of this patent is extended or adjusted under 35 U.S.C. 154(b) by 333 days.

(21) Appl. No.: 12/648,430

(22) Filed: Dec. 29, 2009

(65) Prior Publication Data

US 2010/0166658 A1 Jul. 1, 2010

Related U.S. Application Data

(60) Provisional application No. 61/141,415, filed on Dec. 30, 2008.

(51) Int. Cl.
| | | |
|---|---|---|
| C07K 1/00 | (2006.01) | |
| C07K 14/00 | (2006.01) | |
| C07K 17/00 | (2006.01) | |
| G01N 33/53 | (2006.01) | |
| G01N 33/567 | (2006.01) | |
| G01N 33/566 | (2006.01) | |
| C12P 21/06 | (2006.01) | |
| C12N 1/20 | (2006.01) | |
| C12N 15/74 | (2006.01) | |

(52) U.S. Cl. ......... 530/350; 435/7.1; 435/7.2; 435/69.1; 435/252.3; 435/471; 436/501

(58) Field of Classification Search ............ None
See application file for complete search history.

(56) References Cited

U.S. PATENT DOCUMENTS

| | | | |
|---|---|---|---|
| 5,428,012 A | 6/1995 | Shoyab et al. | |
| 5,571,513 A | 11/1996 | Burstein | |
| 5,618,715 A | 4/1997 | Shoyab et al. | |
| 5,681,930 A | 10/1997 | Radka et al. | |
| 5,792,850 A | 8/1998 | Baumgartner et al. | |
| 5,891,997 A | 4/1999 | Mosley et al. | |
| 5,925,740 A | 7/1999 | Mosley et al. | |
| 5,965,724 A | 10/1999 | Sharkey et al. | |
| 6,706,266 B1 | 3/2004 | Life | |
| 7,534,862 B2 | 5/2009 | Seegert et al. | |
| 2006/0067938 A1 | 3/2006 | Daouti et al. | |
| 2007/0286861 A1 | 12/2007 | Ellis et al. | |
| 2008/0019967 A1 | 1/2008 | Life et al. | |

FOREIGN PATENT DOCUMENTS

| | | |
|---|---|---|
| EP | 1 071 449 B1 | 9/2006 |
| WO | WO 98/18483 A1 | 5/1998 |
| WO | WO 2005/095457 A2 | 10/2005 |

OTHER PUBLICATIONS

Loy JK, et al. Toxicol. Pathol. 27:151-155, 1999.*
Cawston, et al., "The Role of Oncostatin M in Animal and Human Connective Tissue Collagen Turnover and its Localization within the Rheumatoid Joint," Arthritis & Rheymatism, 41(10): 1760-1771 (1998).
Deller, et al., "Crystal structure and functional dissection of the cytostatic cytokine oncostatin M," Structure, 8: 863-874 (2000).
Diveu, et al., "Molecular and Functional Characterization of a Soluble Form of Oncostatin M/Interleukin-31 Shared Receptor," The Journal of Biological Chemistry, 281(48): 36673-36682 (2006).
Kallestad, et al., "Disulfide Bond Assignment and Identification of Regions Required for Functional Activity of Oncostatin M," The Journal of Biological Chemistry, 266(14):8940-8945 (1991).
Saito, et al., "Molecular cloning of a murine IL-6 receptor-associated signal transducer, gp130, and its regulated expression in vivo," The Journal of Immunology, 148: 4066-4071 (1992).

* cited by examiner

*Primary Examiner* — Robert Landsman
(74) *Attorney, Agent, or Firm* — Eric Dichter

(57) ABSTRACT

Cytokine oncostatin M nucleic acids from Cynomolgus monkey are useful for expression of oncostatin M proteins that are functional homologs of human oncostatin M. The nucleic acids and proteins produced therefrom are useful in screening and safety testing of oncostatin M, the generation and testing of oncostatin M modulators and related activities.

6 Claims, 12 Drawing Sheets

FIG. 2

```
          M   G   V   P   L   T   R   R   T   L   L   S   L   I   L   A   L   F   P
  1  ATGGGGGTAC CGCTCACACG GAGGACGCTG CTCAGTCTGA TCCTTGCACT CCTGTTTCCA
          S   M   A   S   M   A   A   M   G   S   C   S   K   E   Y   R   M   L   L   G
 61  AGCATGGCAA GCATGGCGGC TATGGGCAGC TGCTCGAAAG AGTACCGCAT GCTCCTTGGC
          Q   L   Q   K   Q   T   D   L   M   Q   D   T   S   R   L   L   D   P   Y   I
121  CAGCTCCAGA AGCAGACAGA TCTCATGCAG GACACCAGCA GGCTCCTGGA CCCCTATATA
          R   I   Q   G   L   D   I   P   K   L   R   E   H   C   R   E   S   P   G   A
181  CGTATCCAAG GCCTGGATAT TCCTAAACTG AGAGAGCACT GCAGAGAGAG CCCTGGGGCC
          F   P   S   E   E   T   L   R   G   L   G   R   R   G   F   L   Q   T   L   N
241  TTCCCCAGCG AGGAGACCCT GAGGGGGCTG GGCAGGCGGG GCTTCCTACA GACGCTCAAT
          A   T   L   G   R   V   L   H   R   L   A   D   L   E   Q   H   L   P   K   A
301  GCCACACTGG GCCGCGTCCT GCACAGACTG GCCGACTTAG AGCAGCATCT CCCCAAGGCC
          Q   D   L   E   R   S   G   L   N   I   E   D   L   E   K   L   Q   M   A   R
361  CAGGACTTGG AGAGGTCTGG GCTGAACATA GAGGACTTAG AGAAGCTGCA GATGGCGAGG
          P   N   V   L   G   L   R   N   N   I   Y   C   M   A   Q   L   L   D   N   S
421  CCGAATGTCC TCGGGCTCAG GAACAACATC TACTGCATGG CCCAGCTGCT GGACAACTCA
          D   M   T   E   P   T   K   A   G   R   G   T   P   Q   P   P   T   P   T   P
481  GACATGACTG AGCCCACGAA GGCCGGCCGG GGGACCCCTC AGCCGCCCAC CCCCACCCCT
          T   S   D   V   F   Q   R   K   L   E   G   C   S   F   L   R   G   Y   H   R
541  ACCTCAGATG TTTTTCAGCG CAAGCTGGAG GGCTGCAGTT TCCTGCGTGG CTACCATCGC
          F   M   H   S   V   G   R   V   F   S   K   W   G   E   S   P   N   R   S   R
601  TTCATGCACT CAGTGGGGCG GGTCTTCAGC AAGTGGGGGG AGAGCCCGAA CCGGAGCCGG
          R   H   S   P   H   Q   A   L   R   K   G   V   R   R   T   R   P   S   R   K
661  AGACACAGCC CCCACCAGGC CCTGCGGAAG GGGGTGCGCA GGACGAGACC CTCCAGGAAA
          G   N   R   L   M   P   R   G   Q   L   P   R   *
721  GGCAATAGAC TCATGCCCAG GGGACAGCTG CCCCGGTAG
```

FIG. 3A

```
1-100        Human    (1)
ATGGGGGTACTGCTCACACAGAGGACGCTGCTCAGTCTGGTCCTTGCACTCCTGTTTCCAAGCATGGCGAGCATGGCGGCTATA
GGCAGCTGCTCGAAAG Rhesus   (1)
ATGGGGGTACCGCTCACACAGAGGACGCTGCTCAGTCTGATCCTTGCACTCCTGTTTCCAAGCATGGCAAGCATGGCGGCTATG
GGCAGCTGCTCGAAAG Cynomolgus (1)
ATGGGGGTACCGCTCACACGGAGGACGCTGCTCAGTCTGATCCTTGCACTCCTGTTTCCAAGCATGGCAAGCATGGCGGCTATG
GGCAGCTGCTCGAAAG 101-200      Human    (101)
AGTACCGCGTGCTCCTTGGCCAGCTCCAGAAGCAGACAGATCTCATGCAGGACACCAGCAGACTCCTGGACCCCTATATACGTA
TCCAAGGCCTGGATGT Rhesus   (101)
AGTACCGCATGCTCCTTGGCCAGCTCCAGAAGCAGACAGATCTCATGCAGGACACCAGCAGGCTCCTGGACCCCTATATACGTA
TCCAAGGCCTGGATAT Cynomolgus (101)
AGTACCGCATGCTCCTTGGCCAGCTCCAGAAGCAGACAGATCTCATGCAGGACACCAGCAGGCTCCTGGACCCCTATATACGTA
TCCAAGGCCTGGATAT 201-300      Human    (201)
TCCTAAACTGAGAGAGCACTGCAGGGAGCGCCCCGGGGCCTTCCCCAGTGAGGAGACCCTGAGGGGGCTGGGCAGGCGGGGCTT
CCTGCAGACCCTCAAT Rhesus   (201)
TCCTAAACTGAGAGAGCACTGCAGAGAGAGCCCTGGGGCCTTCCCCAGCGAGGAGACCCTGAGGGGGCTGGGCAGGCGGGGCTT
CCTACAGACGCTCAAT Cynomolgus (201)
TCCTAAACTGAGAGAGCACTGCAGAGAGAGCCCTGGGGCCTTCCCCAGCGAGGAGACCCTGAGGGGGCTGGGCAGGCGGGGCTT
CCTACAGACGCTCAAT 301-400      Human    (301)
GCCACACTGGGCTGCGTCCTGCACAGACTGGCCGACTTAGAGCAGCGCCTCCCCAAGGCCCAGGATTTGGAGAGGTCTGGGCTG
AACATCGAGGACTTGG Rhesus   (301)
GCCACACTGGGCCGCGTCCTGCACAGACTGGCCGACTTAGAGCAGCATCTCCCCAAGGCCCAGGACTTGGAGAGGTCTGGGCTG
AACATAGAGGACTTAG Cynomolgus (301)
GCCACACTGGGCCGCGTCCTGCACAGACTGGCCGACTTAGAGCAGCATCTCCCCAAGGCCCAGGACTTGGAGAGGTCTGGGCTG
AACATAGAGGACTTAG
```

*FIG. 3B*

```
401-500     Human     (401)
AGAAGCTGCAGATGGCGAGGCCGAACATCCTCGGGCTCAGGAACAACATCTACTGCATGGCCCAGCTGCTGGACAACTCAGACA
CGGCTGAGCCCACGAA Rhesus    (401)
AGAAGCTGCAGATGGCGAGGCCGAATGTCCTCGGGCTCAGGAACAACGTCTACTGCATGGCCCAGCTGCTGGACAACTCAGACA
TGACTGAGCCCACGAA Cynomolgus (401)
AGAAGCTGCAGATGGCGAGGCCGAATGTCCTCGGGCTCAGGAACAACATCTACTGCATGGCCCAGCTGCTGGACAACTCAGACA
TGACTGAGCCCACGAA 501-600     Human     (501)
GGCTGGCCGGGGGCCTCTCAGCCGCCCACCCCCACCCCTGCCTCGGATGCTTTTCAGCGCAAGCTGGAGGGCTGCAGGTTCCT
GCATGGCTACCATCGC Rhesus    (501)
GGCCGGCCGGGGGACCCCTCAGCCGCCCACCCCCACCCCTACCTCAGATGTTTTTCAGCGCAAGCTGGAGGGCTGCAGTTTCCT
GCGTGGCTACCATCGC Cynomolgus (501)
GGCCGGCCGGGGGACCCCTCAGCCGCCCACCCCCACCCCTACCTCAGATGTTTTTCAGCGCAAGCTGGAGGGCTGCAGTTTCCT
GCGTGGCTACCATCGC 601-700     Human     (601)
TTCATGCACTCAGTGGGGCGGGTCTTCAGCAAGTGGGGGGAGAGCCCGAACCGGAGCCGGAGACACAGCCCCCACCAGGCCCTG
AGGAAGGGGGTGCGCA Rhesus    (601)
TTCATGCACTCAGTGGGGCGGGTCTTCAGCAAGTGGGGGGAGAGCCCGAACCGGAGCCGGAGACACAGCCCCCACCAGGCCCTG
CGGAAGGGGGTGCGCA Cynomolgus (601)
TTCATGCACTCAGTGGGGCGGGTCTTCAGCAAGTGGGGGGAGAGCCCGAACCGGAGCCGGAGACACAGCCCCCACCAGGCCCTG
CGGAAGGGGGTGCGCA 701-759
            Human     (701)
CGACCAGACCCTCCACCAAAGCCAAGAGACTCATCACCAGCCGACACCTGCCCCGGTAC (SEQ ID NO: 6)

Rhesus    (701)
GGACGAGACCCTCCAGGAAAGGCAATAGACTCATGCCCAGGGGACAGCTGCCCCGGTAG (SEQ ID NO: 8)

Cynomolgus (701)
GGACGAGACCCTCCAGGAAAGGCAATAGACTCATGCCCAGGGGACAGCTGCCCCGGTAG (SEQ ID NO: 1)
```

Cyno OSM    (1)    MGVPLTRRTLLSLILALLFPSMASMAAMGSCSKEYRMLLGQLQKQTDLMQ

Human OSM   (1)    MGVLLTQRTLLSLVLALLFPSMASMAAIGSCSKEYRVLLGQLQKQTDLMQ 51-100

Cyno OSM    (51)   DTSRLLDPYIRIQGLDIPKLREHCRESPGAFPSEETLRGLGRRGFLQTLN

Human OSM   (51)   DTSRLLDPYIRIQGLDVPKLREHCRERPGAFPSEETLRGLGRRGFLQTLN 101-150

Cyno OSM    (101)  ATLGRVLHRLADLEQHLPKAQDLERSGLNIEDLEKLQMARPNVLGLRNNI

Human OSM   (101)  ATLGCVLHRLADLEQRLPKAQDLERSGLNIEDLEKLQMARPNILGLRNNI 151-200

Cyno OSM    (151)  YCMAQLLDNSDMTEPTKAGRGTPQPPTPTPTSDVFQRKLEGCSFLRGYHR

Human OSM   (151)  YCMAQLLDNSDTAEPTKAGRGASQPPTPTPASDAFQRKLEGCRFLHGYHR 201-251

Cyno OSM    (201)  FMHSVGRVFSKWGESPNRSRRHSPHQALRKGVRRTRPSRKGNRLMPRGQLPR

Human OSM   (201)  FMHSVGRVFSKWGESPNRSRRHSPHQALRKGVRR*TRPSRKGKRLMTRGQLPR*
``` though

MONKEY HOMOLOG OF HUMAN ONCOSTATIN M AND METHODS OF USE THEREOF

CROSS-REFERENCE TO RELATED APPLICATIONS

This application claims the benefit of priority to U.S. Provisional Application Ser. No. 61/141,415, filed 30 Dec. 2008, the entire contents of which are incorporated herein by reference in their entirety.

FIELD OF THE INVENTION

The present invention relates to oncostatin M, more particularly to a cynomologous monkey homolog of human oncostatin M and its uses.

BACKGROUND OF THE INVENTION

The human Oncostatin M (OSM) gene maps to chromosome 22. Human OSM is expressed as a 252aa polypeptide having a 25 aa signal sequence that is secreted into the extracellular space by epithelial and stromal cells. Proteolytic cleavage near the carboxy-terminus of the mature OSM yields the fully active 209 aa form of OSM having two N-linked glycosylation sites. OSM belongs to the IL-6 family of cytokines that includes (IL-6, IL-11, leukemia inhibitory factor (LIF), cardiotrophin-1, ciliary neutotrophic factor (CNTF) and cardiotrophin-like cytokine (CLC)) which share a common receptor subunit, gp130 protein. In humans, OSM signals through receptor heterodimers consisting of gp130 and the LIFRα subunit or gp130 and the OSMRβ subunit. OSM is produced primarily by cells of immune system origin and, because of the widespread distribution of its signaling receptors, it has been associated with a variety of biological activities, including cell growth regulation, neural development and regulation of extracellular matrix composition.

While human OSM uses both the LIFRα and the OSMRβ to signal, the murine homolog signals only through murine OSMRβ. Thus, the murine protein does not represent a functional surrogate for study of some human OSM pathways.

In addition to the understanding the biological functions of OSM, a need in the art exists to improve current toxicological testing strategies through testing of closely related animal species with human or surrogate biologic proteins. As part of the characterization effort, it is critical to demonstrate reactivity of any therapeutic candidates against the orthologous proteins from available toxicology species, such as cynomologous monkey.

SUMMARY OF THE INVENTION

The invention provides *Macaca fascicularis* polynucleotides and polypeptides. One aspect of the invention is an isolated polynucleotide comprising a polynucleotide having the sequence shown in SEQ ID NO: 1 or a complementary sequence, fragment or variant thereof.

Another aspect of the invention is an isolated polypeptide comprising a polypeptide having the amino acid sequence shown in SEQ ID NO: 2 or a fragment or variant thereof. In one aspect, the fragment is a polypeptide comprising residues 26 to 252 of SEQ ID NO: 2. In another aspect, the fragment is a polypeptide comprising residues 26-234 of SEQ ID NO: 2.

In another embodiment, the invention includes vectors and host cells comprising the polynucleotide having the sequence shown in SEQ ID NO: 1, the sequence encoding the amino acid sequence shown in SEQ ID NO: 2, or a complementary sequence, fragment or variant thereof.

In another embodiment, the polynucleotides of SEQ ID NO: 3, 4, and 5 are used to identify and isolate polynucleotides encoding oncostatin M homologs from cells, tissues, or fluids originating from a host, which host is a member of the order of primates.

In another embodiment, the invention includes antibodies generated using the polynucleotide having the sequence shown in SEQ ID NO: 1 or a complementary sequence, fragment or variant thereof or expressed or isolated polypeptides encoded thereby.

In another embodiment, the polynucleotides, polypeptides, or antibody generated therefrom is used to test the effects of modulating OSM in an *Macaca fascicularis* or other nonhuman primate species of the invention.

BRIEF DESCRIPTION OF THE SEVERAL VIEWS OF THE DRAWING

FIG. 2 shows the cDNA sequence (SEQ ID NO: 10) of *Macaca* OSM with the encoded protein sequence (SEQ ID NO: 2)shown above each codon.

FIGS. 3A and 3B show the nucleotide sequence alignments of the cDNA coding for OSM from Cynomolgus monkey, the predicted Rhesus (*Macaca mulatto*) OSM (NCBI #XM_001110148), and the human sequence.

FIG. 4 shows the predicted polypeptide sequence of cyno OSM aligned with the human OSM sequence, where the human signal peptide is underlined and the human C-terminal pro-peptide is in italics.

BRIEF DESCRIPTION OF THE SEQUENCE LISTING

Figure 1:
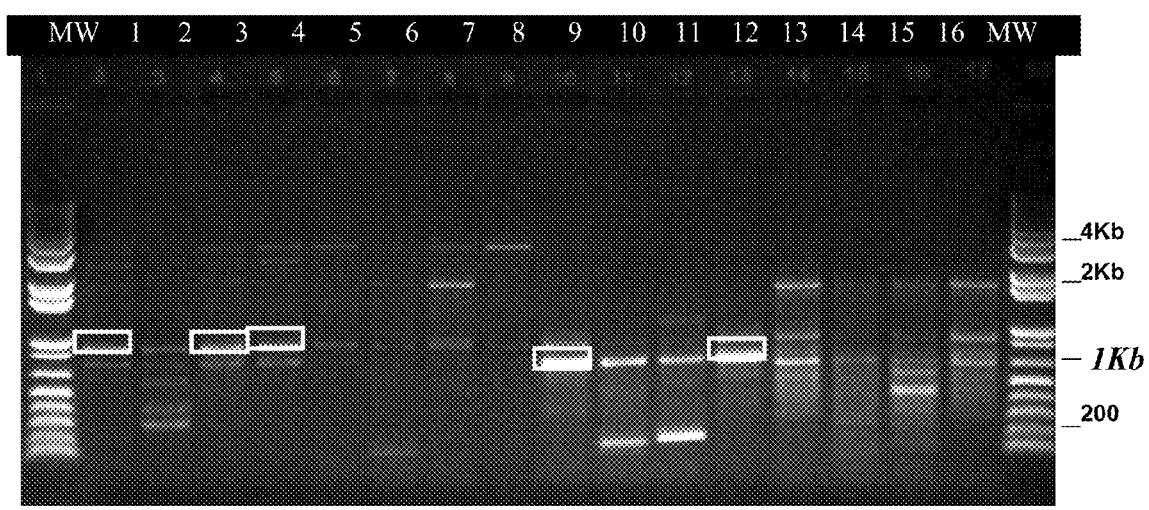
FIG. 1 is an agarose gel electrophoresis showing the separation of PCR products visualized under UV light which showed a band of approximately 1 kB indicated by the white box which was isolated (MW=Molecular Weight marker, lanes 1-16=various combinations of UTR primers with cyno PBMC cDNA template, lane #1 yielded the cyno OSM gene).

| SEQ ID NO: | Description |
|---|---|
| 1 | Cyno OSM coding sequence |
| 2 | Cyno OSM encoded by SEQ ID NO: 1 |
| 3 | Primer |
| 4 | Primer |
| 5 | Primer |
| 6 | Human OSM cDNA |
| 7 | Human OSM polypeptide |
| 8 | Predicted Rhesus OSM cDNA |
| 9 | Predicted Rhesus OSM polypeptide |

DETAILED DESCRIPTION OF THE INVENTION

All publications, including but not limited to patents and patent applications, cited in this specification are herein incorporated by reference as though fully set forth.

Abbreviations

Cyno=Cynomolgus monkey (*Macaca fascicularis*); OSM=oncostatin M; spp.=species; BrdU=5-bromo-2'-deoxyuridine; PBS=phosphate buffered saline; BSA=bovine serum albumin;

Definitions

As used herein, an "antibody" includes whole antibodies and any antigen binding fragment or a single chain thereof. Thus the antibody includes any protein or peptide containing molecule that comprises at least a portion of an immunoglobulin molecule, such as but not limited to at least one complementarity determining region (CDR) of a heavy or light chain or a ligand binding portion thereof, a heavy chain or light chain variable region, a heavy chain or light chain constant region (CH or CL, respectively), a framework (FR) region, or any portion thereof, or at least one portion of a binding protein, which can be incorporated into an antibody of the present invention. The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments to a preselected target. Examples of binding fragments encompassed within the term "antigen binding portion" of an antibody include (i) a Fab fragment, a monovalent fragment consisting of the VL, VH, CL and CH, domains; (ii) a F(ab')2 fragment, a bivalent fragment comprising two Fab fragments linked by a disulfide bridge at the hinge region; (iii) a Fd fragment consisting of the VH and CH, domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (I 988) Science 242:423-426, and Huston et al. (1988) Proc. Natl. Acad Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Conversely, libraries of scFv constructs can be used to screen for antigen binding capability and then, using conventional techniques, spliced to other DNA encoding human germline gene sequences. One example of such a library is the "HuCAL: Human Combinatorial Antibody Library" (Knappik, A. et al. J Mol Biol (2000) 296(1):57-86).

As used herein "OSM" refers to an oncostatin M polypeptide or polynucleotide comprising a coding sequence encoding the OSM polypeptide. Human OSM is the product of the human osm gene (Gene 5008).

The term "epitope" means a protein determinant capable of specific binding to an antibody. Epitopes usually consist of chemically active surface groupings of molecules such as amino acids or sugar side chains and usually have specific three-dimensional structural characteristics, as well as specific charge characteristics. Conformational and nonconformational epitopes are distinguished in that the binding to the former but not the latter is lost in the presence of denaturing solvents.

The term "complementary sequence" means a second isolated polynucleotide sequence that is antiparallel to a first isolated polynucleotide sequence and that comprises nucleotides complementary to the nucleotides in the first polynucleotide sequence. Typically, such "complementary sequences" are capable of forming a double-stranded polynucleotide molecule such as double-stranded DNA or double-stranded RNA when combined under appropriate conditions with the first isolated polynucleotide sequence. Having either a first polynucleotide strand sequence or the antiparallel strand sequence allows immediate recognition of the complementary sequence of one for the other.

The term "polynucleotide" means a molecule comprising a chain of nucleotides covalently linked by a sugar-phosphate backbone or other equivalent covalent chemistry. Double and single stranded DNAs and RNAs are typical examples of polynucleotides. The utility of polynucleotide sequences is their ability to replicate or be replicated in systems using polymerases and be transcribed by ribosomal systems into polypeptides.

The term "vector" means a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. examples of such biological systems may include a cell, virus, animal, plant, and reconstituted biological systems utilizing biological components capable of duplicating a vector. The polynucleotides comprising a vector may be DNA or RNA molecules or hybrids of these.

The term "expression vector" means a vector that can be utilized in a biological system or a reconstituted biological system to direct the translation of a polypeptide encoded by a polynucleotide sequence present in the expression vector.

The term "polypeptide" means a molecule that comprises amino acid residues linked by a peptide bond to form a polypeptide. Small polypeptides of less than 50 amino acids may be referred to as "peptides." Polypeptides may also be referred as "proteins."

By "Cynomolgus monkey" or "cyno" is meant *Macaca fascicularis*. The Cynomolgus monkey is also known as the Crab-Eating Macaque, Long-Tailed Macaque, or Java Macaque. The Rhesus monkey (*Macaca mulatto*) is another member of the macaque genus, which belongs to the family known as Old World Monkeys (Cercopithecidae). Cercopithecidae, Homimidae (including humans and great apes), and Hylobatidae (gibbons) make up a suborder or "clade" within the order of primates, called Catarrhini. Macaques live in many different habitats across the globe, making them the most widely distributed genus of nonhuman primates. Macaques (especially *Macaca mulatta* and *M. fascicularis*) are commonly used in research.

Overview

The present invention provides isolated cynomolgus monkey (*Macaca fascicularis*) OSM polynucleotides, vectors comprising the polynucleotides, isolated host cells, polypeptides obtainable from expression of the polynucleotides, methods for expressing the polypeptides of the invention, and methods of using the polynucleotides and polypeptides of the invention.

The human OSM gene product, OSM (NCBI Accession No. NP_065391) is a pre-pro-polypeptide 252 amino acids in length (SEQ ID NO: 1, FIG. 3), having a signal peptide 25 amino acids in length and a proteolytic cleavage site between residues 234 and 235. It is a secreted protein having five cysteine residues forming two internal disulfides between residues 31 to 152 and 74 to 192 (Kallestad J C, et al. J Biol Chem. 1991 May 15; 266(14):8940-5). There are two potential N-linked glycosylation sites at residues 100 and 217. The human OSM has a free sulfhydryl at residue 105.

The sequence of cyno OSM protein was not available in the public domain although an automated computationally generated record for a 1867 by mRNA (NCBI No. XM_001110148) derived from an annotated genomic sequence (NW_001095169) existed. To obtain the cyno OSM sequence, RNA was isolated from cyno PBMC and the gene was then amplified from this cDNA by RT-PCR and sequenced. The predicted translation of the cloned sequence (SEQ ID NO: 2) was found to be 99.6% identical to the predicted *Macaca mullata* (Rhesus) sequence, 92% identical to the human OSM protein sequence, and 41% identical to the mouse OSM protein sequence.

The fact that there is a greater degree of functional homology between human and cynomologous OSM then between human and mouse suggests that the *Macaca* OSM may be a more relevant a model for human response in experimental studies in vivo than the mouse for evaluation of OSM antagonists, especially antibodies.

Compositions

One aspect of the invention is an isolated polynucleotide comprising a polynucleotide having the sequence shown in SEQ ID NO: 1 or a complementary sequence thereof. The polynucleotide sequence shown in SEQ ID NO: 1 encodes a polypeptide comprising the amino acid sequence as shown in SEQ ID NO: 2, representing the precursor sequence of full length cyno OSM. In one aspect of the invention, the polynucleotide is a truncated form of SEQ ID NO: 1 which encodes the mature form of SEQ ID NO: 2 (without the signal peptide sequence or residues 26-252) such as residues 76-756 of SEQ ID NO: 1. In another aspect, the polynucleotide is a truncated form of SEQ ID NO: 1 comprising nucleotides 1-702 which encodes only residues 1-234 of SEQ ID NO: 2. In another aspect, the polynucleotide of SEQ ID NO: 1 or a fragment thereof is operably linked to a second polynucleotide sequence for the purpose of e.g. expression in a host cell such as an animal, bacterial cell or an insect cell or creating a fusion protein or a "tagged" protein.

The polynucleotides of the invention may also comprise at least one non-coding sequence, such as transcribed but not translated sequences, termination signals, ribosome binding sites, mRNA stabilizing sequences, introns and polyadenylation signals. The polynucleotide sequences may also comprise additional sequences encoding additional amino acids. These additional polynucleotide sequences may, for example, encode a marker or tag sequence such as a hexa-histidine peptide (Gentz et al., Proc. Natl. Acad. Sci. (USA) 86:821-284, 1989) or the HA peptide tag (Wilson et al., Cell 37:767-778, 1984) which facilitate the purification of fused polypeptides.

Another embodiment of the invention is a vector comprising an isolated polynucleotide having a sequence shown in SEQ ID NO: 1 or truncated forms as described herein.

The vectors of the invention are useful for maintaining polynucleotides, duplicating polynucleotides, or driving expression of a polypeptide encoded by a vector of the invention in a biological systems, including reconstituted biological systems. Vectors may be chromosomal-, episomal- and virus-derived such as vectors derived from bacterial plasmids, bacteriophages, transposons, yeast episomes, insertion elements, yeast chromosomal elements, baculoviruses, papova viruses such as SV40, vaccinia viruses, adenoviruses, fowl pox viruses, pseudorabies viruses, picronaviruses and retroviruses and vectors derived from combinations thereof, such as cosmids and phagemids.

The vectors of the invention can be formulated in microparticles, with adjuvants, with lipid, buffer or other excipients as appropriate for a particular application. In one embodiment of the invention the vector is an expression vector. Expression vectors typically comprise nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art. Nucleic acid sequence elements and parent vector sequences suitable for use in the expression of encoded polypeptides are also well known in the art. An exemplary plasmid-derived expression vector useful for expression of the polypeptides of the invention comprises an *E. coli* origin of replication, an aph (3')-1a kanamycin resistance gene, HCMV immediate early promoter with intron A, a synthetic polyA sequence and a bovine growth hormone terminator. Another exemplary plasmid derived expression vector comprises an *E. coli* origin of replication, an ant(4')-1 a kanamycin resistance gene, Rous sarcoma virus long terminal repeat sequences, HCMV immediate early promoter and an SV40 late polyA sequence.

Another embodiment of the invention is an isolated host cell comprising a vector of the invention. Systems for cloning and expression of a polypeptide in a variety of different host cells are well known. Suitable host cells include bacteria, mammalian cells, plant cells, yeast and baculovirus systems and transgenic plants and animals. Mammalian cell lines available in the art for expression of a heterologous polypeptide intact glycosylated proteins include Chinese hamster ovary (CHO) cells, HeLa cells, baby hamster kidney cells (BHK, BHK21, ATCC CRL-10), NSO mouse melanoma cells and derived cell lines, e.g. SP2/0, YB2/0 (ATC CRL-1662) rat myeloma cells, human embryonic kidney cells (HEK, HEK293), human embryonic retina cells PerC.6 cells, hep G2 cells, BSC-1 (e.g., ATCC CRL-26) and many others available from, for example, American Type Culture Collection, Manassas, Va. Populations of cells may comprise an isolated or cultured population of cells or cells present in a matrix such as a tissue.

Mammalian cells such as CHO cells, myeloma cells, BHK cells, mouse Ltk-cells, and NIH3T3 cells have been frequently used for stable expression of heterologous genes. Cell lines such as Cos (COS-1, ATCC CRL 1650; COS-7, ATCC CRL-1651) and HEK293 are routinely used for transient expression of recombinant proteins. A common, preferred bacterial host is *E. coli*.

In another aspect of the invention is an isolated polypeptide comprising the amino acid sequence as shown in SEQ ID NO: 2, variants, and fragments thereof.

The polypeptides of the invention may comprise fusion polypeptides comprising a polypeptide of the invention fused with second polypeptide. Such second polypeptides may be leader or secretory signal sequences, a pre- or pro- or preproprotein sequence, as well as naturally occurring, or partially synthetic sequences derived in part from a naturally occurring sequence or an entirely synthetic sequence. Secretory signal or leader polypeptide sequences may be selected to direct secretion of the polypeptides of the invention into the lumen of the endoplasmic reticulum or extracellular environment; such polypeptide sequences may be heterologous or endogenous to any polypeptide from a primate species or comprise hybrids of these. Exemplary fusion proteins can be formed by conjugating together a macaque polypeptide having an amino acid sequence shown in SEQ ID NO: 2 and one or more domains derived from or similar to an immunoglobulin domain, such as a CH1, CH2, and CH3 domain. In one aspect, the polypeptide represented by the activated polypeptide (residues 26-234) of SEQ ID NO: 2 is fused to an immunoglobulin Fc domain. Such constructs are well known in the art as described in e.g. U.S. Pat. Nos. 5,116,964, 5,709,859, 6,018,026; WO04/002417; WO04/002424; WO05/081687; and WO05/032460. One example of such a related construct is a MIMETIBODY™ construct having the generic formula (I):

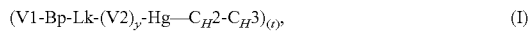
(I)

where Bp is a peptide or polypeptide capable of binding a molecule of interest, Lk is a polypeptide or chemical linkage, V1 and V2 are portions of an immunoglobulin variable regions, Hg is at least a portion of an immunoglobulin variable hinge region, $C_H2$ is an immunoglobulin heavy chain $C_H2$ constant region and $C_H3$ is an immunoglobulin heavy chain $C_H3$ constant region, y is 0 or 1, and t is independently an integer of 1 to 10.

Another embodiment of the invention is an antibody that specifically binds a polypeptide of the invention. The polypeptides of the invention can be used to produce polyclonal or monoclonal antibodies against primate OSM. Techniques for making murine, chimeric, humanized and fully human monoclonal antibodies using protein or nucleic acid immunization are routine and well known to those skilled in the art. Additional discussion and description of such techniques can be found herein below.

Methods of Making the Compositions

The polynucleotides of the invention may be produced by chemical synthesis such as solid phase polynucleotide synthesis on an automated polynucleotide synthesizer and assembled into complete single or double stranded molecules. Alternatively, the polynucleotides of the invention may be produced by other techniques such a PCR based duplication, vector based duplication, or restriction enzyme based DNA manipulation techniques. Techniques for producing or obtaining polynucleotides of a given known sequence are well known in the art.

Introduction of a polynucleotide, such as a vector, into a host cell can be effected by methods well known to those skilled in the art (Davis et al., Basic Methods in Molecular Biology, $2^{nd}$ ed., Appleton & Lange, Norwalk, Conn., 1994; Sambrook et al., Molecular Cloning: A Laboratory Manual, $3^{rd}$ ed., Cold Spring Harbor Laboratory Press, Cold Spring Harbor, N.Y., 2001). These methods include calcium phosphate transfection, DEAE-Dextran mediated transfection, microinjection, cationic lipid-mediated transfection, electroporation, transduction, scrape loading, ballistic introduction and infection.

The polypeptides of the invention may be produced by chemical synthesis, such as solid phase peptide synthesis, on an automated peptide synthesizer. Alternatively, the polypeptides of the invention can be obtained from polynucleotides encoding these polypeptides by the use of cell-free expression systems such as reticulocyte lystate based expression systems, wheat germ extract based expression systems, and *Escherichia coli* extract based expression systems. The polypeptides of the invention can also be obtained by expression and isolation from cells harboring a nucleic acid sequence of the invention by techniques well known in the art, such as recombinant expression of easily isolated affinity labeled polypeptides. Those skilled in the art will recognize other techniques for obtaining the polypeptides of the invention.

Another embodiment of the invention is a method for expressing a polypeptide comprising the steps of providing a host cell of the invention; culturing the host cell under conditions sufficient for the expression of a polypeptide comprising the sequence shown in SEQ ID NO: 2 or a variant or fragment thereof; and confirming expression of the polypeptide, variant, or fragment thereof.

In the methods of the invention, the expression of a polypeptide can be confirmed using a variety of different techniques well known in the art. Detection of the polypeptide of the expected molecular weight using chromatographic techniques or electrophoretic techniques are well known in the art. In order to confirm that the polypeptide comprise the correct primary, secondary, tertiary or higher order structure other techniques must be employed. For example, expression of a polypeptide can be confirmed using detection reagents, such as antibodies or receptor ligands, specific for an expressed polypeptide. Antibodies that specifically bind to or cross-react with the cyno OSM polypeptides of the invention are one example of such reagents. Detection reagents may be detectably labeled by conjugation or incorporation of a radiolabel, fluorophore, chromophore, an enzyme capable of causing a detectable signal to be produced, or other detectable molecule to, or into, the detection reagent.

Expression of a polypeptide can also be confirmed by assaying for a biological activity associated with OSM, such as the ability to regulate tumor cell growth in vitro or in vivo.

Methods of Using the Invention

In one embodiment of the invention, the isolated polypeptide of SEQ ID NO: 2 or a fragment thereof is used as an immunogen to elicit or "raise" antibodies in a host such as a rabbit, mouse, rat, guinea pig, or goat. In another embodiment, isolated polypeptide of SEQ ID NO: 2 or a fragment thereof may be used to interrogate a library to select molecules capable of binding the polypeptide or fragment thereof. It will be recognized that host cells engineered to with the polynucleotides of SEQ ID NO: 1 or a fragment thereof or a vector comprising such as polynucleotide may also be used for such purposes. In a particular aspect of using the isolated polypeptide of SEQ ID NO: 2 or a fragment thereof is used to select immunoglobulin fragments from a library of such fragments.

In one embodiment of the invention, the polypeptide epitope for binding of an antibody specific for or raised against cyno OSM is determined by a method known in the art such as those described Chapter 11 of Harlow, E. (Ed.), Using antibodies: A Laboratory Manual, 1999. Cold Spring Harbor Laboratory Press, Cold Spring Harbor, N.Y. pp. 379-405. The epitope sequence and or structure may be compared to other natural homologs or variants or the ability of the antibody to block specific biological functions or binding to receptors can be assessed so that a relationship between the polypeptide sequence or structure at the epitope can be related to the biological functions contributed by the epitope or domain of the OSM polypeptide.

Another embodiment of the invention is a method of determining cross-reactivity of an OSM modulator with cyno OSM. Even if the polypeptides and epitopes are preserved across species and in the species under consideration for a predictive model for a modulator, cross-reactivity of a modulator should be established before additional experimentation is performed (Loisel et al., Crit. Rev. in One. Hematol. 62:34-42, 2007). Cross-reactivity of modulators, antibodies of the invention and OSM antibodies to selected based on reactivity to species homolog polypeptides and other antigens may be assayed using, for example, competitive and non-competitive assay systems using techniques such as BIAcore analysis, FACS, analysis, immunofluorescence, immunocytochemistry, radioimmunoassays, ELISA, "sandwich" immunoassays, immunoprecipitation assays, western blots, immunoradiometric assays, fluorescent immunoassays, and protein A immunoassays. Such assays are routine and well known in the art and can be found described in e.g. the Current Protocols series of manuals, published by John Wiley & Sons, Inc., New York and updated regularly. Cross-reactivity can also be evaluated by assaying for inhibition of a biological activity associated with activation of OSM. Additional discussion of such assays can be found in Harlow (supra).

Another embodiment of the invention is a method for determining if an OSM modulator is likely to be safe or unsafe for use in humans comprising providing an OSM modulator, a first *Macaca* spp. monkey (Macaque), and a second *Macaca* spp. monkey; administering the OSM modulator to the first *Macaca* spp. monkey; and determining whether the first *Macaca* spp. monkey is presenting a deleterious symptom relative to the second monkey, where presentation of a deleterious symptom by the first *Macaca* spp. monkey shows the OSM modulator is potentially unsafe for use in humans and a lack of presentation of a deleterious symptom by the first *Macaca* spp. monkey shows the OSM therapeutic is potentially safe in humans.

In the methods of the invention the determination of whether the first *Macaca* spp. monkey is presenting a deleterious symptom relative to the second *Macaca* spp. monkey is readily accomplished. For example, a person of ordinary skill in the art such as a veterinarian, veterinarian's assistant, animal technician, or research scientist can determine if a symptom presented by an animal is deleterious. examples of deleterious symptoms include death, coma, seizures, fever, organ failure, tissue abnormalities, impaired organ function, impaired tissue function, cancers, tumors, ulcers, bleeding, anemia, infections, paralysis, pain, erythema, dermatitis and the like.

The present invention will now be described with reference to the following specific, non-limiting examples.

EXAMPLE 1

Cloning of CYNO OSM

Untranslated region (UTR) primers for the 5' and 3' ends were designed using the human OSM sequence (NCBI accession #NM_020530, SEQ ID NO: 6) as shown in Table 1. Cyno PBMC's were obtained from blood sample from Cynomolgus monkeys and RNA was made using Qiagen Rneasy mini-kit (#74104) and the Qiagen Qiashredder kit (#79654). Next, cDNA was generated from the PBMC RNA using Superscript III first strand synthesis system (InVitrogen, #18080-051). The cDNA was then PCR amplified using the UTR primers designed from the human OSM sequence.

TABLE 1

| Description | Oligo sequence | SEQ ID NO: |
|---|---|---|
| 5' UTR huOSM#1 | 5'-agccgagaggtgtcaccc-3' | 3 |
| 3' UTR huOSM#1 | 5'-cctctcatccacagagc-3' | 4 |
| M13 Forward (-20) | 5'-gtaaaacgacggccagt-3' | 5 |

PCR product was separated by 1% agarose TBE agarose gel electrophoresis and visualized under UV light. A fragment of approximately 1 kB was expected; the band indicated by the white box in lane #2 of FIG. 1 yielded the cyno OSM gene using SEQ ID NO: 3 and 4. The band of about 1 kB was extracted using the Qiagen Qiaquick gel extraction kit (#28706). The PCR product contained full-length sequence as well as some 5' and 3' UTR. The band was then cloned into the pCR4 TOPO-TA vector using TOPO kit (InVitrogen, #K4575-01). The transformation product was plated on Carb-75 agar plates and incubated overnight at 37° C. The next day, eight colonies per plate were picked and used to inoculate 2 ml LB amp100 media, which were then grown over night at 37 C. Miniprep DNA was then created using the Qiagen Qiaprep turbo 96-miniprep kit (#27191). The DNA was then sequenced using the M13 Forward primer (-20, SEQ ID NO: 5) and analyzed using the ABI 3100 sequencer.

The cyno OSM clone #1 polynucleotide sequence (FIG. 2, SEQ ID NO: 1) demonstrated homology (99.6%) to the Rhesus predicted OSM sequence (NCBI accession #XM_001110148, SEQ ID NO: 8) as shown in FIG. 3A-B. The cyno protein product (SEQ ID NO: 2) was 99.2% identical to the predicted Rhesus sequence (SEQ ID NO: 9), differing only by I150V from cyno to rhesus in the mature chain. The cyno OSM amino acid translation of the coding sequence gives a polypeptide having 92.1% identity to the human OSM sequence over the full length (20 residue differences) as shown in FIG. 4. The cyno OSM is predicted to have only 4 cysteine residues which represent those participating in the two intramolecular disulfide bonds but no free cysteine.

Other OSM homologs have been identified and the translation products noted including mouse (NP_001013383, 263 aa); rat (NP_001006962, 239 aa); bovine (NP_783644, 245 aa); and a predicted sequence for chimpanzee (XP_001136178, 252 aa); Rhesus XP_001110148); and dog (XP_854737, 268 aa). An identity table comparing the proteins pairwise using the Clustal W algorithm is shown in Table 2. The mouse and rat OSM homologs have the lowest identity to other homologs of all presently known or predicted sequences.

TABLE 2

| Homolog | Cyno | Chimp | Dog | Bovine | Rat | Mouse |
|---|---|---|---|---|---|---|
| human | 92.1 | 99.2 | 51.4 | 51.3 | 48.2 | 40.9 |
| Chimpanzee | 92.1 | | | | | |
| Dog | 50.0 | 51.8 | | | | |
| Bovine | 51.3 | 51.7 | 50.6 | | | |
| Rat | 47.8 | 47.8 | 37.9 | 39.2 | | |
| Mouse | 40.9 | 40.5 | 36.4 | 37.7 | 58.4 | |

EXAMPLE 2

Expression and Activity of CYNO OSM

HEK 293-F cells were seeded at $5.0 \times 10^5$ cells per ml in a Wave Cellbag 20L (GE # CB0020L) the day prior to transfection in 10 L of 293 FreeStyle media (Invitrogen #12338). The settings for the Wave bioreactor were 18 rocks per minute at a 7 degree angle with 0.3 L/min of air set at 8.0% $CO_2$ and 37° C. On the day of transfection, the cells were at $1.0 \times 10^6$ cells per ml. An aliquot of a mixture containing 6.25 mg of OSMA2 DNA encoding Cyno Oncostatin M-His-Avi with 6.25 mg of pAdvantage (Promega #E1711) was diluted in 100 ml of Opti-Pro media (Invitrogen #12309). Max Transfection Reagent, 12.5 ml, was diluted in 100 ml of Opti-Pro media and the DNA and lipid were combined and allowed to incubate for 10 minutes at room temperature. Then, 200 ml of the DNA lipid complex was added to the cells and the rocking speed was increased to 28 RPM while the other conditions were held constant. Incubation continued for 96 hours.

Cyno OSM was purified from the supernatant using immobilized metal-chelate affinity chromatography (IMAC) on an AKTA FPLC chromatography system controlled by GE Healthcare Unicorn™ software. Cell supernatants were clarified by centrifugation (30 min, 6000 rpm), filtered (0.2 μm PES membrane, Corning) and concentrated 10-fold using an LV Centramate (Pall) concentrator. The concentrated supernatant was then diluted with 10×PBS to a final concentration of 1×PBS, and again 0.2 μm filtered. Diluted supernatant was loaded onto an equilibrated (20 mM Na-Phosphate, 0.5M NaCl, pH7.4) HisTrap column (GE Healthcare) at a relative concentration of about 10 mg protein per ml of resin. After loading, the column was washed and protein eluted with a step gradient of Imidazole (10, 50, 150, 250 and 500 mM). The total volume used for each step of the elution was equal to 10 column volumes. Peak fractions were pooled and concentrated. The concentrated peak fractions were then loaded onto a Superdex 200 column (GE Healthcare) equilibrated with PBS (pH7) for size exclusion chromatography. Fractions containing the Cyno OSM-His-Avi were pooled and filtered (0.2 μm). Total protein concentration was determined by absorbance at 280 nm using a BioTek Synergy HT plate reader. The purified protein was concentrated with a 10K molecular weight cut-off (MWCO) centrifugal concentrator (Millipore). The quality of the purified protein was assessed by SDS-PAGE and HPLC-SEC. From this pool, 6 mg of Cyno OSM-His-Avi at 40 mM concentration were dialyzed into 10 mM Tris-HCl, pH 8 and supplemented for biotinylation with 50 mM Bicine, 10 mM ATP, 10 mM MgOAc, 50 mM biotin and 206 mg of biotin ligase (Avidity). After 3 hours at 37° C., the biotinylated Cyno OSM-His-Avi was purified by IMAC using NiNTA Superflow resin (Qiagen) and dialyzed back into PBS (pH 7). The quality of the purified protein was again assessed by SDS-PAGE and HPLC-SEC.

Figure 5:
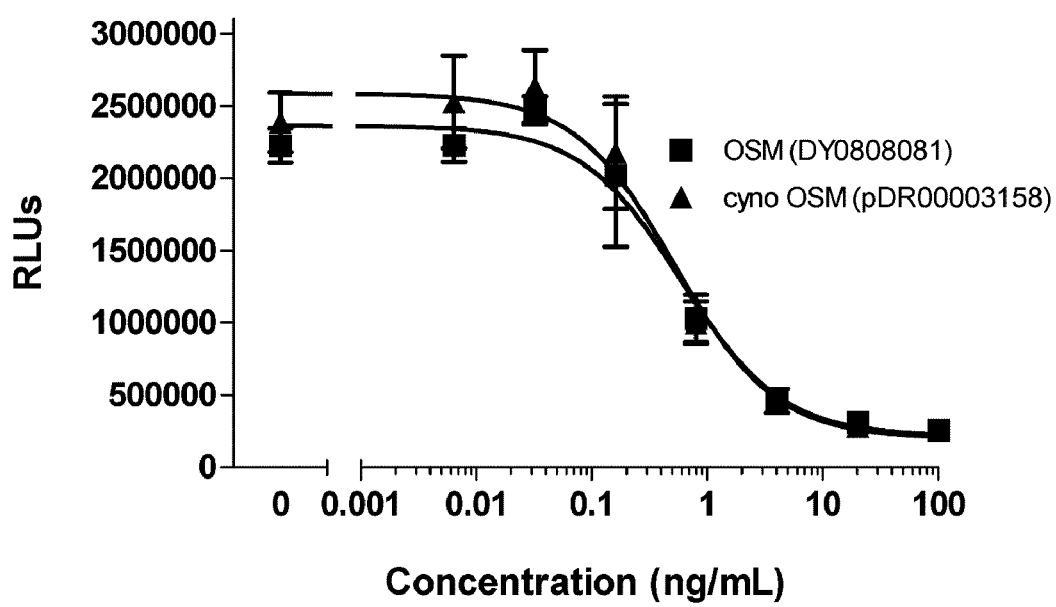
FIG. 5 shows the bioactivity of the cloned and expressed cyno OSM (▲) protein as compared to commercially produced human OSM (■).

A375 cells (ATCC, CRL-1619) are a human melanoma-derived cell line that responds to human OSM by reducing the rate of proliferation (Zarling et al. (1986) Oncostatin M: a growth regulator produced by differentiated histiocytic lymphoma cells PNAS 83:9739-9743) were used to determine the activity of the expressed and purified cynomologous monkey OSM described above. FIG. 5 shows the effect of commercially available recombinant human OSM (R&D Systems 295-OM) and purified cynomologous monkey OSM (expressed as described above) on BrdU incorporation in cultures of A375 cells. The cells were seeded at 2000 cells/well in 200 mL of DMEM w/High Glucose (Gibco 10303) with 10% heat-inactivated FBS (Gibco 16140) and cultured for 24 hours. At that time, human and cyno OSM were prepared at 10× in PBS (Sigma Aldrich D8537) with 1% BSA (Gibco 15260). The media bathing the A375 cultures was replaced with 180 microL of fresh media and 20 microL of the appropriate 10× solution was added to each well to expose the cells to various concentrations of either human or cyno OSM. After 64 hours of treatment, proliferation was quantified using a BrdU proliferation kit (Cell Proliferation ELISA, BrdU (chemiluminescent), Roche Applied Science, USA, #11669915001). BrdU reagent was added directly to the cultures and incubated for 4 hours. The media was then removed and anti-BrdU with conjugated peroxidase was added. After washing out un-bound antibody, the proprietary substrate was added and the amount of incorporated BrdU was quantified in a luminometer. Both human and cyno OSM decreased BrdU incorporation in a concentration-dependent manner with nearly identical EC50 values: 0.59 ng/ml (human, squares) and 0.53 ng/ml (cyno, triangles).

EXAMPLE 3

STAT3 Phosphorylation Activity of CYNO OSM

The purified protein was tested in a STAT3 phosphorylation assay using immortalized cyno lung fibroblasts and A375 cells.

Cells are maintained in DMEM (Gibco Cat #11995)+10% FBS (Gibco Cat #16140)+1% Pen/Strep (Gibco Cat #15140). Cells are cultured in DMEM+10% FBS. This is also the assay media. In black TC-treated plates, 25,000 cells/well are plated in the first 9 columns of a 96 well plate in their normal growth media. The outer wells are filled with 200 μL of PBS to prevent evaporation. The cells are incubated overnight at 37° C.

The following day, for cytokine growth curves the media is completely removed and 180 μL of fresh media is added (done per plate so that wells do not dry out). A dilution plate is made in media with 10× concentrations of agonists (such as OSM) and 1:4 dilutions from 1000 to 0.02 ng/mL. Then, 20 μL is added to triplicate wells of the assay plate.

After 10 minute incubation, the supernatant is removed by vacuum and 100 μL of complete lysis buffer (RIPA buffer plus protease and phosphatase inhibitors) is added to each well in the same order as the addition of the treatment solutions. The assay plate is then placed on a shaker for 10 minutes. After 10 minutes of shaking, the lysates are applied directly to the pre-coated anti-pSTAT3 ELISA plate, or frozen at −80° C. for later testing. The ELISA was performed according to the instructions of the R&D Systems protocol with the following changes: To account for possible volume losses during lysate prep and transfer to ELISA plate, only 90 μL of lysate or standard was added to each well of the ELISA plate. SuperSignal Pico is used to as the HRP substrate (chemiluminescence)

Figure 6:
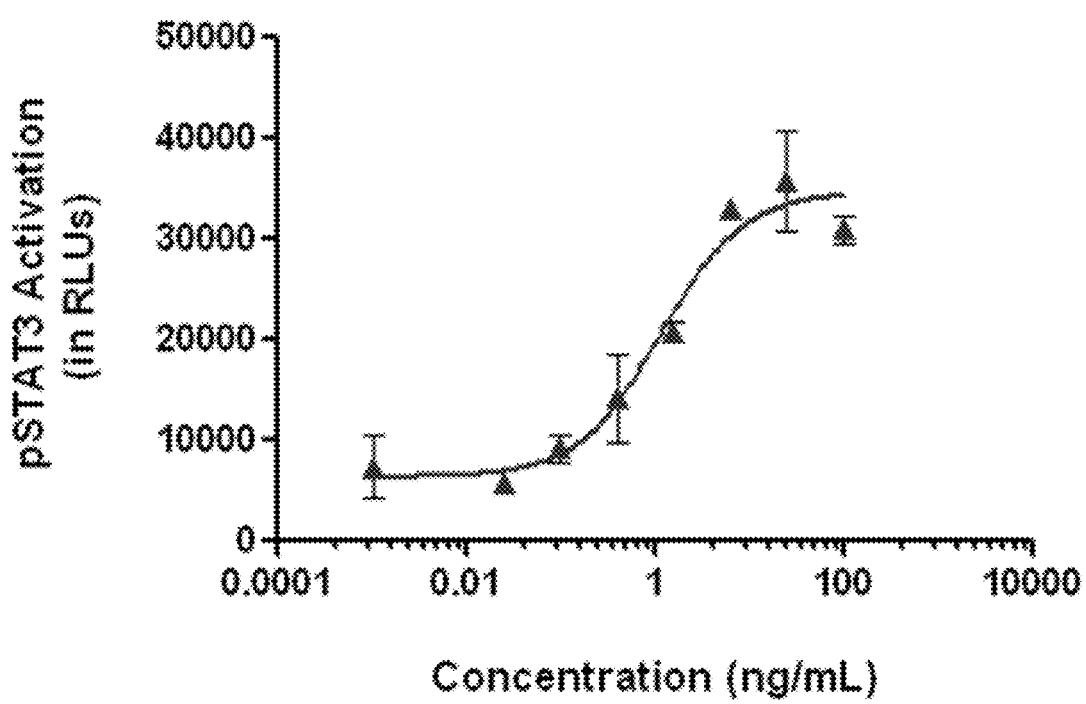
FIG. 6 shows HEK-expressed cyno OSM inducing STAT3 phosphorylation in immortalized cyno lung fibroblasts.
Figure 7A:
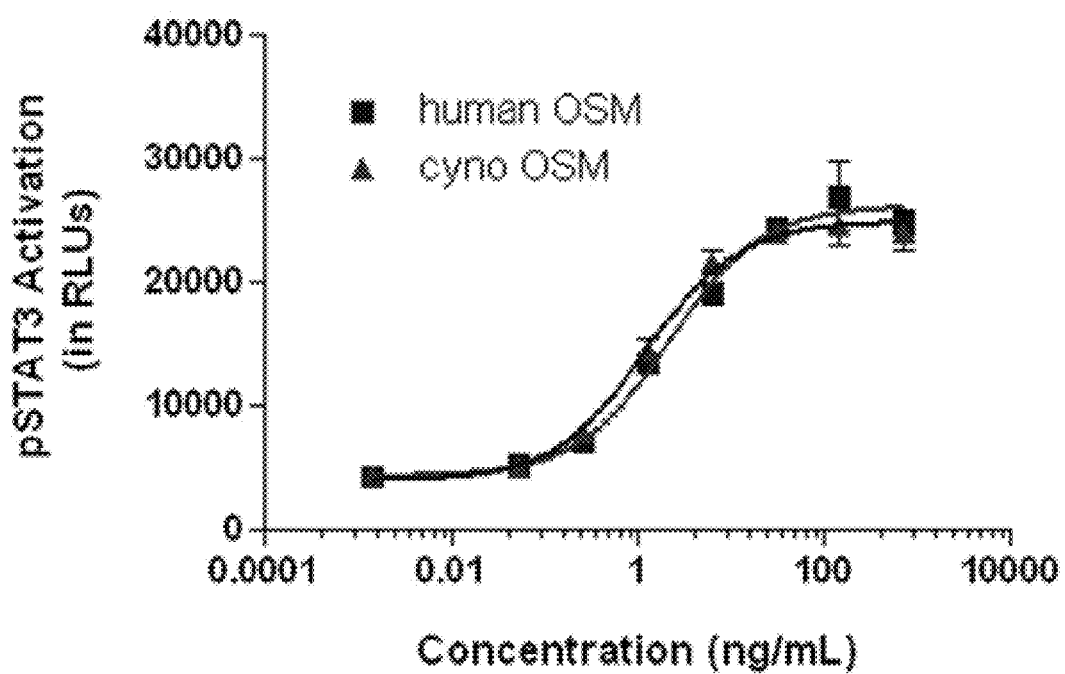
FIGS. 7A and 7B show the comparative activity of cyno and human OSM on A375 cells.
Figure 7B:
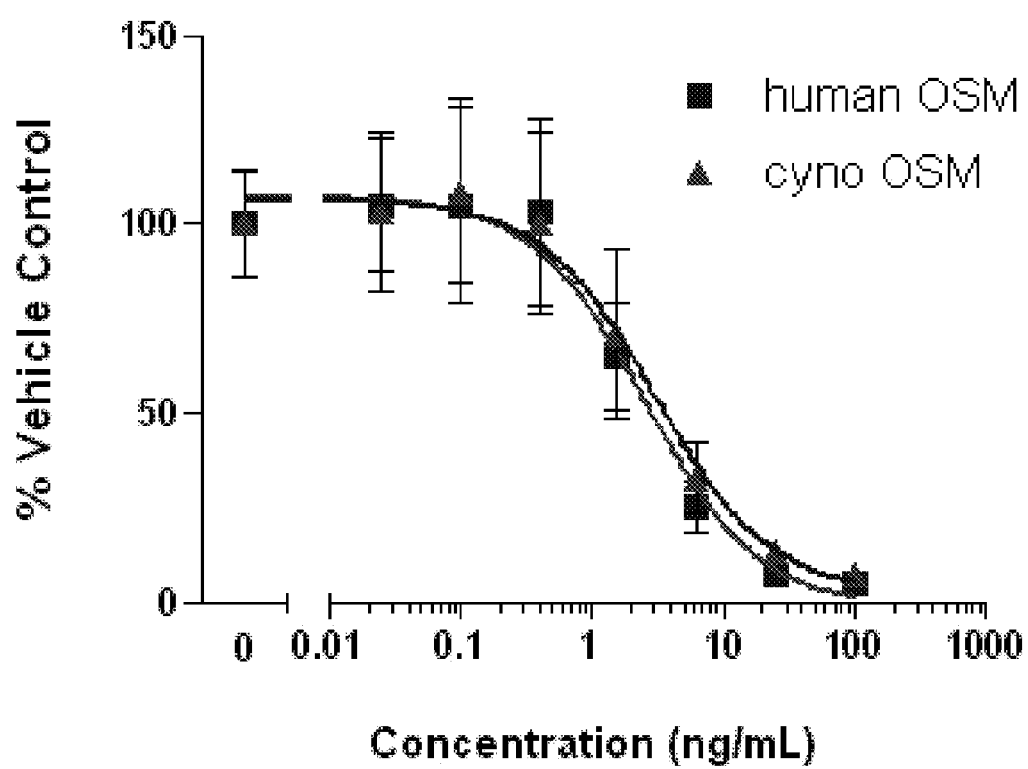

FIG. 6 shows that HEK-expressed cyno OSM induces STAT3 phosphorylation in immortalized cyno lung fibroblasts in a concentration dependent manner. The $EC_{50}$ for this activity is approximately 1.1 ng/mL. FIG. 7A shows the induction of STAT3 phosphorylation in A375 cells by human and cyno recombinant OSM. Both recombinant proteins induce STAT3 phosphorylation in a concentration dependent manner, with the $EC_{50}$ of human OSM being 0.6118 and for cyno OSM 0.3681 ng/mL. FIG. 7B shows the effects of recombinant human and cyno OSM on the proliferation of A375 cells. Both proteins inhibited the proliferation of cells in a concentration dependent manner. The $EC_{50}$ of human OSM is 2.556 and for cyno OSM is 3.022.

EXAMPLE 4

Collagen Synthesis Assay

NHLF are plated at a concentration of 8,000 cells/well in 96-well TC plates and cultured overnight in growth medium (FGM-2 Lonza). The cells are treated with IL-13 (5 ng/ml), and either TGF-B1 (1, 0.1 ng/ml, or 0.05 ng/ml), or increasing concentrations of cyno OSM. The next day, cells are re-stimulated with cyno OSM as in the previous day, along with 20 ug/ml ascorbid acid overnight. The cells are fixed with 95% ethanol, and processed for human collagen I ELISA.

Figure 8A:
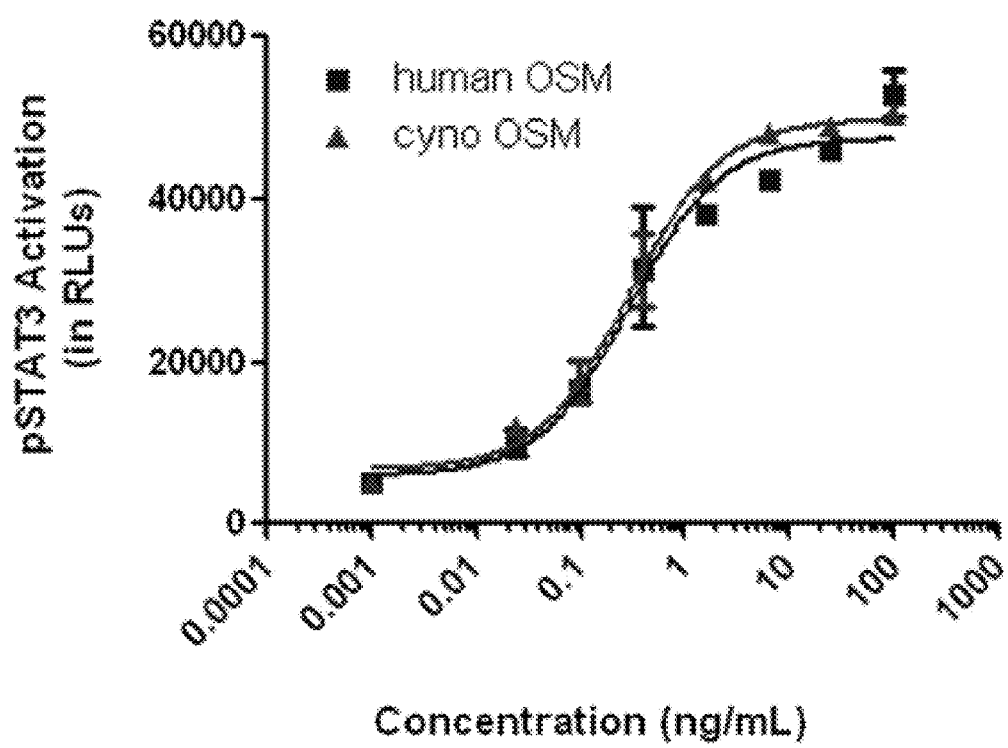
FIGS. 8A and 8B show the activity of cyno OSM in NHLF cells.
Figure 8B:
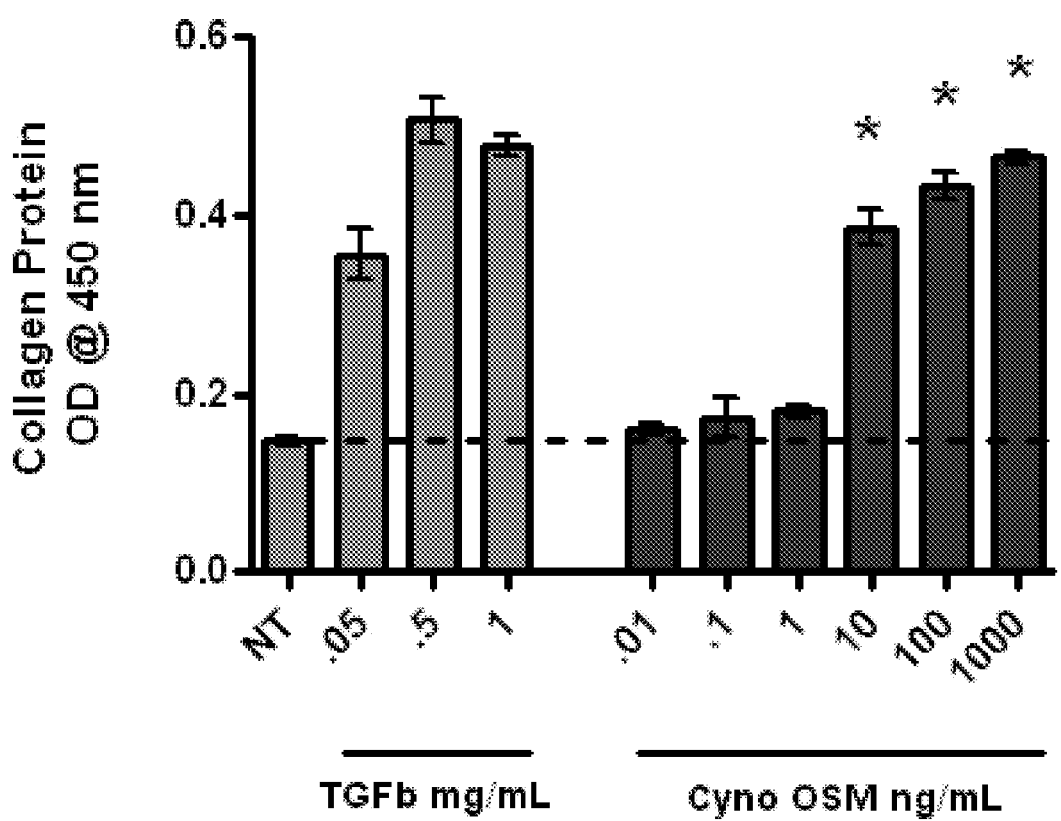

FIG. 8B shows the effect of cyno OSM on collagen synthesis (NT=no treatment). Cyno OSM induced collagen synthesis in a concentration dependent manner, similar to TGF-B1, a known stimulator of collagen synthesis.

EXAMPLE 5

Proteoglycan Synthesis Assay

Figure 9:
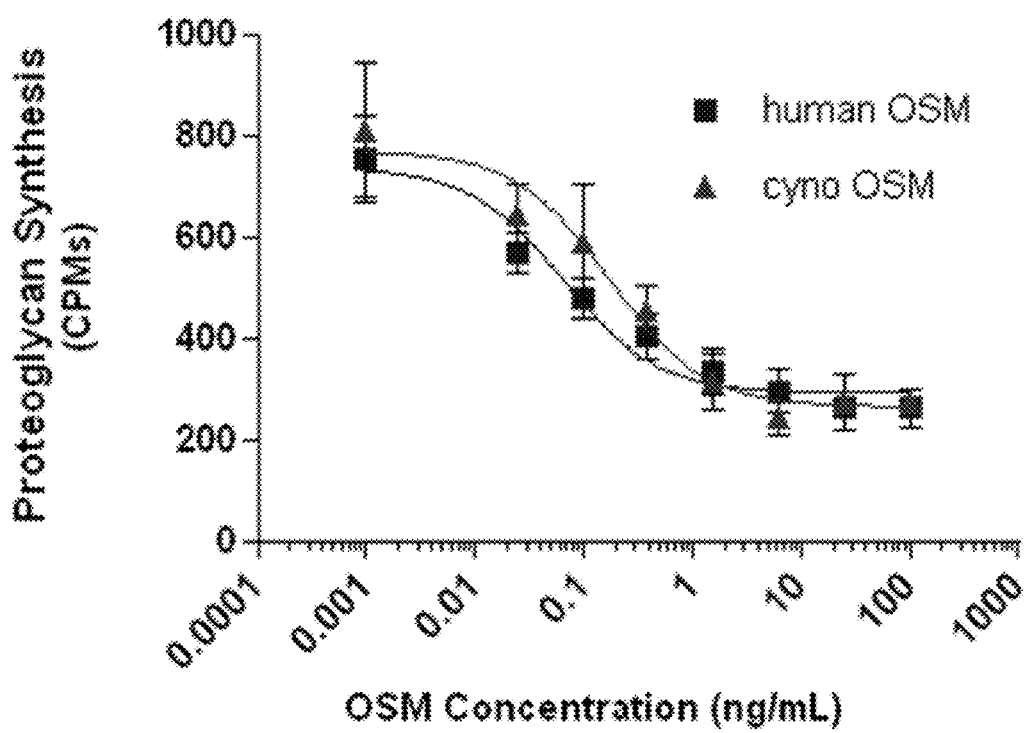
FIG. 9 shows that cyno and human OSM decrease proteoglycan synthesis by human chondrocytes.

The purified protein was tested in a proteoglycan synthesis assay using human chondrocytes. Primary human chondrocytes were received from Articular Engineering encapsulated in alginate at 40,000 cells/bead. 1 bead/well was plated into a 96 well plate. Beads were treated with a dose range of oncostatin M, or 2 ng/mL oncostatin M± a dose range of OSM antibody. After 48 hours, the media was replaced to include treatment plus 10 µCi/mL $^{35}$S to measure glycosaminoglycan (GAG) synthesis. The following day, the beads were washed to remove unincorporated $^{35}$S, and then digested with papain for analysis. FIG. 9 shows that cyno and human OSM decrease proteoglycan synthesis by human chondrocytes in vitro.

---

SEQUENCE LISTING

<160> NUMBER OF SEQ ID NOS: 10

<210> SEQ ID NO 1
<211> LENGTH: 756
<212> TYPE: DNA
<213> ORGANISM: Macaca fascicularis

<400> SEQUENCE: 1

```
atgggggtac cgctcacacg gaggacgctg ctcagtctga tccttgcact cctgtttcca      60
agcatggcaa gcatggcggc tatgggcagc tgctcgaaag agtaccgcat gctccttggc     120
cagctccaga agcagacaga tctcatgcag gacaccagca ggctcctgga ccctatata     180 cgtatccaag gcctggatat tcctaaactg agagagcact gcagagagag ccctggggcc     240
ttccccagcg aggagaccct gaggggggctg ggcaggcggg gcttcctaca gacgctcaat     300
gccacactgg gccgcgtcct gcacagactg gccgacttag agcagcatct ccccaaggcc     360
caggacttgg agaggtctgg gctgaacata gaggacttag agaagctgca gatggcgagg     420
ccgaatgtcc tcgggctcag gaacaacatc tactgcatgg cccagctgct ggacaactca     480
gacatgactg agcccacgaa ggccggccgg gggaccctc agccgcccac ccccaccct     540 acctcagatg tttttcagcg caagctggag ggctgcagtt tcctgcgtgg ctaccatcgc     600
ttcatgcact cagtggggcg ggtcttcagc aagtgggggg agagcccgaa ccggagccgg     660
agacacagcc cccaccaggc cctgcggaag ggggtgcgca ggacgagacc ctccaggaaa     720
ggcaatagac tcatgcccag gggacagctg ccccgg                                756
```

<210> SEQ ID NO 2
<211> LENGTH: 252
<212> TYPE: PRT
<213> ORGANISM: Macaca fascicularis

<400> SEQUENCE: 2

```
Met Gly Val Pro Leu Thr Arg Arg Thr Leu Leu Ser Leu Ile Leu Ala
1               5                   10                  15

Leu Leu Phe Pro Ser Met Ala Ser Met Ala Ala Met Gly Ser Cys Ser
                20                  25                  30

Lys Glu Tyr Arg Met Leu Leu Gly Gln Leu Gln Lys Gln Thr Asp Leu
            35                  40                  45

Met Gln Asp Thr Ser Arg Leu Leu Asp Pro Tyr Ile Arg Ile Gln Gly
        50                  55                  60

Leu Asp Ile Pro Lys Leu Arg Glu His Cys Arg Glu Ser Pro Gly Ala
65                  70                  75                  80

Phe Pro Ser Glu Glu Thr Leu Arg Gly Leu Gly Arg Arg Gly Phe Leu
                85                  90                  95

Gln Thr Leu Asn Ala Thr Leu Gly Arg Val Leu His Arg Leu Ala Asp
```

```
                    100                 105                 110
Leu Glu Gln His Leu Pro Lys Ala Gln Asp Leu Glu Arg Ser Gly Leu
            115                 120                 125

Asn Ile Glu Asp Leu Glu Lys Leu Gln Met Ala Arg Pro Asn Val Leu
        130                 135                 140

Gly Leu Arg Asn Asn Ile Tyr Cys Met Ala Gln Leu Leu Asp Asn Ser
145                 150                 155                 160

Asp Met Thr Glu Pro Thr Lys Ala Gly Arg Gly Thr Pro Gln Pro Pro
                165                 170                 175

Thr Pro Thr Pro Thr Ser Asp Val Phe Gln Arg Lys Leu Glu Gly Cys
            180                 185                 190

Ser Phe Leu Arg Gly Tyr His Arg Phe Met His Ser Val Gly Arg Val
        195                 200                 205

Phe Ser Lys Trp Gly Glu Ser Pro Asn Arg Ser Arg Arg His Ser Pro
210                 215                 220

His Gln Ala Leu Arg Lys Gly Val Arg Arg Thr Arg Pro Ser Arg Lys
225                 230                 235                 240

Gly Asn Arg Leu Met Pro Arg Gly Gln Leu Pro Arg
                245                 250

<210> SEQ ID NO 3
<211> LENGTH: 18
<212> TYPE: DNA
<213> ORGANISM: Homo sapiens

<400> SEQUENCE: 3
agccgagagg tgtcaccc                                                   18

<210> SEQ ID NO 4
<211> LENGTH: 17
<212> TYPE: DNA
<213> ORGANISM: Homo sapiens

<400> SEQUENCE: 4
cctctcatcc acagagc                                                    17

<210> SEQ ID NO 5
<211> LENGTH: 17
<212> TYPE: DNA
<213> ORGANISM: Homo sapiens

<400> SEQUENCE: 5
gtaaaacgac ggccagt                                                    17

<210> SEQ ID NO 6
<211> LENGTH: 759
<212> TYPE: DNA
<213> ORGANISM: Homo sapiens

<400> SEQUENCE: 6
atgggggtac tgctcacaca gaggacgctg ctcagtctgg tccttgcact cctgtttcca     60
agcatggcga gcatggcggc tataggcagc tgctcgaaag agtaccgcgt gctccttggc    120
cagctccaga agcagacaga tctcatgcag gacaccagca gactcctgga cccctatata    180
cgtatccaag gcctggatgt tcctaaactg agagagcact gcagggagcg ccccggggcc    240
ttccccagtg aggagaccct gaggggggctg ggcaggcggg gcttcctgca gaccctcaat    300
gccacactgg gctgcgtcct gcacagactg gccgacttag agcagcgcct ccccaaggcc    360
caggatttgg agaggtctgg gctgaacatc gaggacttgg agaagctgca gatggcgagg    420
```

```
ccgaacatcc tcgggctcag gaacaacatc tactgcatgg cccagctgct ggacaactca    480
gacacggctg agcccacgaa ggctggccgg ggggcctctc agccgcccac ccccacccct    540
gcctcggatg cttttcagcg caagctggag ggctgcaggt tcctgcatgg ctaccatcgc    600
ttcatgcact cagtggggcg ggtcttcagc aagtgggggg agagcccgaa ccggagccgg    660
agacacagcc cccaccaggc cctgaggaag ggggtgcgca ggaccagacc ctccaggaaa    720
ggcaagagac tcatgaccag gggacagctg ccccggtag                          759
```

<210> SEQ ID NO 7
<211> LENGTH: 252
<212> TYPE: PRT
<213> ORGANISM: Homo sapiens

<400> SEQUENCE: 7

```
Met Gly Val Leu Leu Thr Gln Arg Thr Leu Ser Leu Val Leu Ala
1               5                   10                  15

Leu Leu Phe Pro Ser Met Ala Ser Met Ala Ala Ile Gly Ser Cys Ser
            20                  25                  30

Lys Glu Tyr Arg Val Leu Leu Gly Gln Leu Gln Lys Gln Thr Asp Leu
        35                  40                  45

Met Gln Asp Thr Ser Arg Leu Leu Asp Pro Tyr Ile Arg Ile Gln Gly
    50                  55                  60

Leu Asp Val Pro Lys Leu Arg Glu His Cys Arg Glu Arg Pro Gly Ala
65                  70                  75                  80

Phe Pro Ser Glu Glu Thr Leu Arg Gly Leu Gly Arg Arg Gly Phe Leu
                85                  90                  95

Gln Thr Leu Asn Ala Thr Leu Gly Cys Val Leu His Arg Leu Ala Asp
            100                 105                 110

Leu Glu Gln Arg Leu Pro Lys Ala Gln Asp Leu Glu Arg Ser Gly Leu
        115                 120                 125

Asn Ile Glu Asp Leu Glu Lys Leu Gln Met Ala Arg Pro Asn Ile Leu
    130                 135                 140

Gly Leu Arg Asn Asn Ile Tyr Cys Met Ala Gln Leu Leu Asp Asn Ser
145                 150                 155                 160

Asp Thr Ala Glu Pro Thr Lys Ala Gly Arg Gly Ala Ser Gln Pro Pro
                165                 170                 175

Thr Pro Thr Pro Ala Ser Asp Ala Phe Gln Arg Lys Leu Glu Gly Cys
            180                 185                 190

Arg Phe Leu His Gly Tyr His Arg Phe Met His Ser Val Gly Arg Val
        195                 200                 205

Phe Ser Lys Trp Gly Glu Ser Pro Asn Arg Ser Arg Arg His Ser Pro
    210                 215                 220

His Gln Ala Leu Arg Lys Gly Val Arg Arg Thr Arg Pro Ser Arg Lys
225                 230                 235                 240

Gly Lys Arg Leu Met Thr Arg Gly Gln Leu Pro Arg
                245                 250
```

<210> SEQ ID NO 8
<211> LENGTH: 759
<212> TYPE: DNA
<213> ORGANISM: Macaca mulatta

<400> SEQUENCE: 8

```
atggggg tac cgctcacaca gaggacgctg ctcagtctga tccttgcact cctgtttcca     60
agcatggcaa gcatggcggc tatgggcagc tgctcgaaag agtaccgcat gctccttggc    120
```

```
cagctccaga agcagacaga tctcatgcag gacaccagca ggctcctgga cccctatata    180
cgtatccaag gcctggatat tcctaaactg agagagcact gcagagagag ccctggggcc    240
ttccccagcg aggagaccct gaggggggctg ggcaggcggg gcttcctaca gacgctcaat    300
gccacactgg gccgcgtcct gcacagactg gccgacttag agcagcatct ccccaaggcc    360
caggacttgg agaggtctgg gctgaacata gaggacttag agaagctgca gatggcgagg    420
ccgaatgtcc tcgggctcag gaacaacgtc tactgcatgg cccagctgct ggacaactca    480
gacatgactg agcccacgaa ggccggccgg gggacccctc agccgcccac ccccaccccct    540 acctcagatg ttttttcagcg caagctggag ggctgcagtt tcctgcgtgg ctaccatcgc    600
ttcatgcact cagtgggggcg ggtcttcagc aagtggggggg agagcccgaa ccggagccgg    660
agacacagcc cccaccaggc cctgcggaag ggggtgcgca ggacgagacc ctccaggaaa    720
ggcaatagac tcatgcccag gggacagctg ccccggtag                           759
```

```
<210> SEQ ID NO 9
<211> LENGTH: 252
<212> TYPE: PRT
<213> ORGANISM: Macaca mulatta

<400> SEQUENCE: 9

Met Gly Val Pro Leu Thr Gln Arg Thr Leu Leu Ser Leu Ile Leu Ala
1               5                   10                  15

Leu Leu Phe Pro Ser Met Ala Ser Met Ala Ala Met Gly Ser Cys Ser
                20                  25                  30

Lys Glu Tyr Arg Met Leu Leu Gly Gln Leu Gln Lys Gln Thr Asp Leu
            35                  40                  45

Met Gln Asp Thr Ser Arg Leu Leu Asp Pro Tyr Ile Arg Ile Gln Gly
        50                  55                  60

Leu Asp Ile Pro Lys Leu Arg Glu His Cys Arg Glu Ser Pro Gly Ala
65                  70                  75                  80

Phe Pro Ser Glu Glu Thr Leu Arg Gly Leu Gly Arg Arg Gly Phe Leu
                85                  90                  95

Gln Thr Leu Asn Ala Thr Leu Gly Arg Val Leu His Arg Leu Ala Asp
            100                 105                 110

Leu Glu Gln His Leu Pro Lys Ala Gln Asp Leu Glu Arg Ser Gly Leu
        115                 120                 125

Asn Ile Glu Asp Leu Glu Lys Leu Gln Met Ala Arg Pro Asn Val Leu
130                 135                 140

Gly Leu Arg Asn Asn Val Tyr Cys Met Ala Gln Leu Leu Asp Asn Ser
145                 150                 155                 160

Asp Met Thr Glu Pro Thr Lys Ala Gly Arg Gly Thr Pro Gln Pro Pro
                165                 170                 175

Thr Pro Thr Pro Thr Ser Asp Val Phe Gln Arg Lys Leu Glu Gly Cys
            180                 185                 190

Ser Phe Leu Arg Gly Tyr His Arg Phe Met His Ser Val Gly Arg Val
        195                 200                 205

Phe Ser Lys Trp Gly Glu Ser Pro Asn Arg Ser Arg Arg His Ser Pro
    210                 215                 220

His Gln Ala Leu Arg Lys Gly Val Arg Thr Arg Pro Ser Arg Lys
225                 230                 235                 240

Gly Asn Arg Leu Met Pro Arg Gly Gln Leu Pro Arg
                245                 250
```

-continued

```
<210> SEQ ID NO 10
<211> LENGTH: 759
<212> TYPE: DNA
<213> ORGANISM: Macaca fascicularis

<400> SEQUENCE: 10
atgggggtac cgctcacacg gaggacgctg ctcagtctga tccttgcact cctgtttcca      60
agcatggcaa gcatggcggc tatgggcagc tgctcgaaag agtaccgcat gctccttggc     120
cagctccaga agcagacaga tctcatgcag gacaccagca ggctcctgga cccctatata     180
cgtatccaag gcctggatat tcctaaactg agagagcact gcagagagag ccctggggcc     240
ttccccagcg aggagaccct gaggggggctg ggcaggcggg gcttcctaca gacgctcaat     300
gccacactgg gccgcgtcct gcacagactg gccgacttag agcagcatct cccaaggcc      360 caggacttgg agaggtctgg gctgaacata gaggacttag agaagctgca gatggcgagg     420
ccgaatgtcc tcgggctcag gaacaacatc tactgcatgg cccagctgct ggacaactca     480
gacatgactg agcccacgaa ggccggccgg gggacccctc agccgccac cccaccct      540 acctcagatg tttttcagcg caagctggag ggctgcagtt tcctgcgtgg ctaccatcgc     600
ttcatgcact cagtggggcg ggtcttcagc aagtgggggg agagcccgaa ccggagccgg     660
agacacagcc cccaccaggc cctgcggaag ggggtgcgca ggacgagacc ctccaggaaa     720
ggcaatagac tcatgcccag gggacagctg ccccggtag                             759
```

What is claimed:

1. An isolated polypeptide comprising a polypeptide having the sequence shown in SEQ ID NO: 2 from residues 26 to 234.

2. An isolated polypeptide comprising a polypeptide having the sequence shown in SEQ ID NO: 2 from residues 1 to 234.

3. An isolated polypeptide comprising a polypeptide having the sequence shown in SEQ ID NO: 2.

4. A method for determining cross-reactivity of a human OSM (SEQ ID NO: 6) modulator with cyno OSM comprising:
   a. providing an OSM modulator and a cyno OSM isolated polypeptide comprising the sequence shown in SEQ ID NO: 2 from residues 26 to 234;
   b. contacting the OSM modulator with the cyno OSM isolated polypeptide; and
   c. determining whether the OSM modulator binds to the cyno OSM isolated polypeptide.

5. A method for determining cross-reactivity of a human OSM modulator with cyno OSM comprising:
   a. providing an OSM modulator and an isolated host cell comprising an expression vector having a polynucleotide as shown in SEQ ID NO: 1;
   b. expressing a cyno OSM isolated polypeptide comprising the sequence shown in SEQ ID NO:2 from residues 26 to 234;
   c. contacting the OSM modulator with the expressed cyno OSM polypeptide; and
   d. determining the effect of the OSM modulator on OSM activity, wherein modulation of OSM activity resulting from contacting the OSM modulator shows that the OSM therapeutic cross-reacts with the cyno OSM.

6. The method of claim 5, wherein the OSM modulator is an antibody, an antibody portion or fragment, a peptide, a polypeptide, an oligonucleotide, or a combination thereof.

* * * * *